United States Patent [19]

Cohen et al.

[11] Patent Number: 5,314,737
[45] Date of Patent: May 24, 1994

[54] AREA THINNED THIN SHEET MATERIALS

[75] Inventors: Bernard Cohen, Berkley Lake; Lee K. Jameson, Roswell, both of Ga.

[73] Assignee: Kimberly-Clark Corporation, Neenah, Wis.

[21] Appl. No.: 767,727

[22] Filed: Sep. 30, 1991

[51] Int. Cl.$^5$ .............................................. B32B 3/00
[52] U.S. Cl. ..................................... 428/156; 428/141; 428/212; 428/213; 428/215; 428/218; 428/913
[58] Field of Search ............... 428/156, 172, 212, 141, 428/178, 213, 215, 218, 304.4, 913

[56] References Cited

U.S. PATENT DOCUMENTS

| Re. 33,063 | 9/1989 | Obeda | 156/73.1 |
|---|---|---|---|
| 1,982,587 | 11/1934 | Wilkins | 204/6 |
| 2,289,177 | 7/1942 | Chandler | 154/43 |
| 2,533,609 | 12/1950 | Nolan et al. | 18/47.5 |
| 2,740,184 | 4/1956 | Thomas | 28/78 |
| 3,025,585 | 3/1962 | Griswold | 28/1 |
| 3,097,149 | 7/1963 | Lacroix | 204/146 |
| 3,155,460 | 11/1964 | Mears | 29/183.5 |
| 3,253,317 | 5/1966 | Such | 28/76 |
| 3,333,032 | 7/1967 | Dickinson | 264/22 |
| 3,352,769 | 11/1967 | Ruben | 204/143 |
| 3,400,188 | 9/1968 | Olson | 264/156 |
| 3,451,884 | 6/1969 | Anno et al. | 161/53 |
| 3,488,240 | 1/1970 | Roberts | 156/73 |
| 3,571,679 | 3/1971 | VanTurnhout | 317/262 |
| 3,575,752 | 4/1971 | Carpenter | 156/73 |
| 3,594,134 | 7/1971 | Russell et al. | 29/191.4 |
| 3,635,609 | 1/1972 | Balamuth | 425/3 |
| 3,640,786 | 2/1972 | Carpenter | 156/73 |
| 3,642,967 | 2/1972 | Doll | 264/51 |
| 3,660,186 | 5/1972 | Sager et al. | 156/73 |
| 3,683,736 | 8/1972 | Loose | 83/16 |
| 3,713,960 | 1/1973 | Cochran, II | 161/66 |
| 3,723,754 | 3/1973 | Murayama et al. | 307/88 ET |
| 3,756,880 | 9/1973 | Graczyk | 156/73 |
| 3,794,174 | 2/1974 | Booman et al. | 210/321 |
| 3,814,101 | 6/1974 | Kozak | 128/287 |
| 3,818,522 | 6/1974 | Schuster | 5/347 |
| 3,832,267 | 8/1974 | Liu | 161/116 |
| 3,881,489 | 5/1975 | Hartwell | 128/287 |
| 3,886,941 | 6/1975 | Duane et al. | 128/287 |
| 3,929,135 | 12/1975 | Thompson | 128/287 |
| 3,949,127 | 4/1976 | Ostermeier et al. | 428/137 |

(List continued on next page.)

FOREIGN PATENT DOCUMENTS

| 0141556 | 5/1985 | European Pat. Off. . |
|---|---|---|
| 0195113 | 9/1986 | European Pat. Off. . |
| 0203820 | 12/1986 | European Pat. Off. . |
| 0256717A2 | 2/1988 | European Pat. Off. . |
| 0259003 | 3/1988 | European Pat. Off. . |
| 0302611A1 | 2/1989 | European Pat. Off. . |

(List continued on next page.)

OTHER PUBLICATIONS

"Ultrasonics/High Power", Kirk-Othmer *Encyclopedia of Chemical Technology*, vol. 23, pp. 462-479, ©1983.
"Crop Control", *Modern Plastics*, May 1991, pp. 58-60.
European Search Report 92 11 6585; counterpart of U.S. Serial No. 07/769,047.
European Search Report 92 11 6586; counterpart of U.S. Serial No. 07/768,782.
European Search Report 92 11 6573; counterpart of U.S. Serial No. 07/768,494.
European Search Report 92 11 6587; counterpart of

(List continued on next page.)

Primary Examiner—Donald J. Loney
Attorney, Agent, or Firm—Joseph P. Harps

[57] ABSTRACT

A method for forming thinned areas in a thin sheet material. The method includes the steps of (1) placing the thin sheet material on a pattern anvil having a pattern of raised areas wherein the height of the raised areas is generally less than the thickness of the sheet material; (2) conveying the sheet material, while placed on the pattern anvil, through an area where a fluid is applied to the sheet material; and (3) subjecting the sheet material to a sufficient amount of ultrasonic vibrations in the area where the fluid is applied to the sheet material to area thin the sheet material in a pattern generally the same as the pattern of raised areas on the pattern anvil. In some embodiments, the thinned areas may be micro areas.

55 Claims, 6 Drawing Sheets

U.S. PATENT DOCUMENTS

| | | | |
|---|---|---|---|
| 3,956,450 | 5/1976 | Abe et al. | 264/21 OR |
| 3,963,309 | 6/1976 | Schwab | 350/104 |
| 3,966,519 | 6/1976 | Mitchell et al. | 156/73.1 |
| 3,989,867 | 11/1976 | Sisson | 428/132 |
| 3,998,916 | 12/1976 | VanTurnhout | 264/22 |
| 4,028,033 | 6/1977 | Bryant | 425/183 |
| 4,105,724 | 8/1978 | Talbot | 261/112 |
| 4,215,682 | 8/1980 | Kubik et al. | 128/205.29 |
| 4,242,392 | 12/1980 | Yackiw | 428/85 |
| 4,311,542 | 1/1982 | Mueller et al. | 156/84 |
| 4,369,219 | 1/1983 | Goepp et al. | 428/138 |
| 4,375,718 | 3/1983 | Wadsworth et al. | 29/592 |
| 4,389,211 | 6/1983 | Lenaghan | 604/383 |
| 4,406,720 | 9/1983 | Wang et al. | 156/73.2 |
| 4,414,045 | 11/1983 | Wang et al. | 156/73.2 |
| 4,414,244 | 11/1983 | Timberlake et al. | 427/105 |
| 4,438,167 | 3/1984 | Schwarz | 428/138 |
| 4,439,475 | 3/1984 | Lang | 428/92 |
| 4,472,328 | 9/1984 | Sugimoto et al. | 264/41 |
| 4,488,928 | 12/1984 | Ali Khan et al. | 156/495 |
| 4,588,537 | 5/1986 | Klaase et al. | 264/22 |
| 4,592,815 | 6/1986 | Nakao | 204/165 |
| 4,601,868 | 7/1986 | Radel et al. | 264/504 |
| 4,605,454 | 8/1986 | Sayovitz et al. | 156/73.1 |
| 4,609,518 | 9/1986 | Curro et al. | 264/504 |
| 4,623,438 | 11/1986 | Felton et al. | 204/168 |
| 4,629,643 | 12/1986 | Curro et al. | 428/131 |
| 4,645,500 | 2/1987 | Steer | 604/378 |
| 4,695,422 | 9/1987 | Curro et al. | 264/504 |
| 4,731,282 | 3/1988 | Tsukagoshi et al. | 428/220 |
| 4,735,843 | 4/1988 | Noda | 428/137 |
| 4,747,895 | 5/1988 | Wallerstein et al. | 156/73.3 |
| 4,775,571 | 10/1988 | Mizuno et al. | 428/141 |
| 4,777,073 | 10/1988 | Sheth | 428/155 |
| 4,778,644 | 10/1988 | Curro et al. | 264/557 |
| 4,798,604 | 1/1989 | Carter | 604/383 |
| 4,801,379 | 1/1989 | Ehrsam et al. | 210/498 |
| 4,815,714 | 3/1989 | Douglas | 264/22 |
| 4,842,794 | 6/1989 | Hovis et al. | 264/145 |
| 4,898,761 | 2/1990 | Dunaway et al. | 428/137 |
| 4,900,317 | 2/1990 | Buell | 604/370 |
| 4,929,319 | 5/1990 | Dinter et al. | 204/164 |
| 4,931,343 | 6/1990 | Becker et al. | 428/95 |
| 4,944,854 | 7/1990 | Felton et al. | 204/168 |
| 4,955,164 | 9/1990 | Hashish et al. | 51/321 |
| 4,980,215 | 12/1990 | Schonbrun | 428/72 |
| 4,995,930 | 2/1991 | Merz et al. | 156/209 |
| 5,015,521 | 5/1991 | Fujii et al. | 428/220 |
| 5,059,454 | 10/1991 | Todd et al. | 427/259 |
| 5,098,755 | 3/1992 | Tanquary et al. | 428/161 |
| 5,116,662 | 5/1992 | Morman | 428/198 |
| 5,225,018 | 7/1993 | Zeldin et al. | 156/167 |

FOREIGN PATENT DOCUMENTS

| | | |
|---|---|---|
| 3723404A1 | 1/1989 | Fed. Rep. of Germany. |
| 1334711 | 9/1962 | France. |
| 5038-755 | 12/1975 | Japan. |
| 1018971 | 2/1966 | United Kingdom. |
| 1073605 | 6/1967 | United Kingdom. |
| 1253664 | 11/1971 | United Kingdom. |
| 2124134B | 2/1984 | United Kingdom. |
| 2218990A | 11/1989 | United Kingdom. |

OTHER PUBLICATIONS

U.S. Serial No. 07/769,045; 07/769,048; 07/768,788 and 07/769,048.

European Search Report 92 11 9574; counterpart of U.S. Serial No. 07/767,727.

"Recent Progress in Electret Research", *Topics in Applied Physics*, vol. 33, 2nd ed., 1987, pp. 383–431.

*Electrets and Related Electrostatic Charge Storage Phenomena*, ©1968 by The Electrochemical Society, Inc.

*Sonochemistry: The Uses of Ultrasound in Chemistry*, Mason, T. J., Royal Society of Chemistry, pp. 83, 85.

Translation of Japanese Patent Application No. HEI 3(1991)-260160.

AREA THINNED THIN SHEET MATERIALS

RELATED APPLICATIONS

This application is one of a group of applications which are being filed on the same date. It should be noted that this group of applications includes U.S. patent application Ser. No. 07/769,050 entitled "Hydrosonically Microapertured Thin Thermoset Sheet Materials" in the names of Lee K. Jameson and Bernard Cohen; U.S. patent application Ser. No. 07/769,047 entitled "Hydrosonically Microapertured Thin Thermoplastic Sheet Materials" in the names of Bernard Cohen and Lee K. Jameson; U.S. patent application Ser. No. 07/768,782 entitled "Pressure Sensitive Valve System and Process For Forming Said System" in the names of Lee K. Jameson and Bernard Cohen; U.S. patent application Ser. No. 07/768,494 entitled "Hydrosonically Embedded Soft Thin Film Materials and Process For Forming Said Materials" in the names of Bernard Cohen and Lee K. Jameson; U.S. patent application Ser. No. 07/768,788 entitled "Hydrosonically Microapertured Thin Naturally Occurring Polymeric Sheet Materials and Method of Making the Same" in the names of Lee K. Jameson and Bernard Cohen; U.S. patent application Ser. No. 07/769,048 entitled "Hydrosonically Microapertured Thin Metallic Sheet Materials" in the names of Bernard Cohen and Lee K. Jameson; U.S. patent application Ser. No. 07/769,045 entitled "Process For Hydrosonically Microaperturing Thin Sheet Materials" in the names of Lee K. Jameson and Bernard Cohen; and U.S. patent application Ser. No. 07/767,727 entitled "Process For Hydrosonically Area Thinning Thin Sheet Materials" in the names of Bernard Cohen and Lee K. Jameson. All of these applications are hereby incorporated by reference.

FIELD OF THE INVENTION

The field of the present invention encompasses processes for area thinning thin sheet materials in a generally uniform pattern and the area thinned thin sheet materials formed thereby.

BACKGROUND OF THE INVENTION

Ultrasonics is basically the science of the effects of sound vibrations beyond the limit of audible frequencies. Ultrasonics has been used in a wide variety of applications. For example, ultrasonics has been used for (1) dust, smoke and mist precipitation; (2) preparation of colloidal dispersions; (3) cleaning of metal parts and fabrics; (4) friction welding; (5) the formation of catalysts; (6) the degassing and solidification of molten metals; (7) the extraction of flavor oils in brewing; (8) electroplating; (9) drilling hard materials; (10) fluxless soldering and (10) nondestructive testing such as in diagnostic medicine.

The object of high power ultrasonic applications is to bring about some permanent physical change in the material treated. This process requires the flow of vibratory power per unit of area or volume. Depending on the application, the power density may range from less than a watt to thousands of watts per square centimeter. Although the original ultrasonic power devices operated at radio frequencies, today most operate at 20-69 kHz.

The piezoelectric sandwich-type transducer driven by an electronic power supply has emerged as the most common source of ultrasonic power; the overall efficiency of such equipment (net acoustic power per electric-line power) is typically greater than 70%. The maximum power from a conventional transducer is inversely proportional to the square of the frequency. Some applications, such as cleaning, may have many transducers working into a common load.

Other, more particular areas where ultrasonic vibratory force has been utilized are in the areas of thin nonwoven webs and thin films. For example, ultrasonic force has been use to bond or weld nonwoven webs. See, for example, U.S. Pat. No. 3,575,752 to Carpenter, U.S. Pat. No. 3,660,186 to Sager et al., U.S. Pat. No. 3,966,519 to Mitchell et al. and U.S. Pat. No. 4,605,454 to Savovitz et al. which disclose the use of ultrasonics to bond or weld nonwoven webs. U.S. Pat. No. 3,488,240 to Roberts, describes the use of ultrasonics to bond or weld thin films such as oriented polyesters.

Ultrasonic force has also been utilized to aperture nonwoven webs. See, for example, U.S. Pat. No. 3,949,127 to Ostermeier et al. and U.S. Pat. No. 3,966,519 to Mitchell et al..

Lastly, ultrasonic force has been used to aperture thin film material. See, for example, U.S. Pat. No. 3,756,880 to Graczyk.

Other methods for the aperturing of thin film have been developed. For example, U.S. Pat. No. 4,815,714 to Douglas discusses the aperturing of a thin film by first abrading the film, which is in filled and unoriented form, and then subjecting the film to corona discharge treatment.

One of the difficulties and obstacles in the use of ultrasonic force in the formation of apertures in materials is the fact that control of the amount of force which is applied was difficult. This lack of control resulted in the limitation of ultrasonic force to form large apertures as opposed to small microapertures. Such an application is discussed in U.K. patent application number 2,124,134 to Blair. One of the possible reasons that ultrasonics has not found satisfactory acceptance in the area of microaperture formation is that the amount of vibrational energy required to form an aperture often resulted in a melt-through of the film.

As has previously been stated, those in the art had recognized that ultrasonics could be utilized to form apertures in nonwoven webs. See, U.S. patent to Mitchell, et al.. Additionally, the Mitchell et al. patent discloses that the amount of ultrasonic energy being subjected to a nonwoven web could be controlled by applying enough of a fluid to the area at which the ultrasonic energy was being applied to the nonwoven web so that the fluid was present in uncombined form. Importantly, the Mitchell, et al. patent states that the fluid is moved by the action of the ultrasonic force within the nonwoven web to cause aperture formation in the web by fiber rearrangement and entanglement. The Mitchell et al. patent also states that, in its broadest aspects, since these effects are obtained primarily through physical movement of fibers, the method of their invention may be utilized to bond or increase the strength of a wide variety of fibrous webs.

While the discovery disclosed in the Mitchell et al. patent, no doubt, was an important contribution to the art, it clearly did not address the possibility of area thinning of nonfibrous thin sheet materials or thin sheet materials having fibers in such a condition that they could not be moved or rearranged. This fact is clear because the Mitchell et al. patent clearly states the belief that the mechanism of aperture formation depended upon fiber rearrangement. Of course, such thin sheet materials do not have fibers which can be rearranged. Accordingly, it can be stated with conviction that the applicability of a method for area thinning such thin sheet materials by the application of ultrasonic energy in conjunction with a fluid at the point of application of the ultrasonic energy to the sheet material was not contemplated by the Mitchell et al. patent. Moreover, the Mitchell et al. patent teaches away from such an application because the patent states the belief that aperture formation (physical effects) requires the presence of fibers to be rearranged.

Another area of interest to the present invention is the area of barrier fabrics. Barrier fabrics are utilized in a variety of areas. For example, chemical workers sometimes wear garments made from a barrier fabric which seeks to protect the worker from harmful materials which he may become exposed to. Likewise, operating room personnel typically wear garments which are designed to protect the patient from germs that the personnel may carry and also protect the operating room personnel from germs, viruses etc. that the patient may harbor. While many barrier fabrics have been designed, one of the more difficult aspects of the creation of barrier fabrics which are to be used to make garments is to make the fabric "breathable". In other words, for the comfort of the wearer, it is highly desirable for the fabric to act as a barrier to the potentially harmful substance that it is designed to block while still allowing the passage of air and water vapor. Otherwise, the garment may well quickly turn into a "hot box". Accordingly, it has long been a goal of those in the art to produce a barrier fabric which is "breathable" but, a the same time, provides adequate protection against the harmful substance which is to be maintained at a distance.

DEFINITIONS

As used herein the term "sheet material" refers to a generally nonporous item that can be arranged in generally planar configuration which, in an unthinned state, prior to being modified in accordance with the present invention, has a hydrostatic pressure (hydrohead) of at least about 100 centimeters of water when measured in accordance with Federal Test Method NO. 5514, standard no. 191A. This term is also intended to include multilayer materials which include at least one such sheet as a layer thereof.

As used herein the term "thin sheet material" refers to a sheet material having an average thickness generally of less than about ten (10) mils. Average thickness is determined by randomly selecting five (5) locations on a given sheet material, measuring the thickness of the sheet material at each location to the nearest 0.1 mil, and averaging the five values (sum of the five values divided by five).

As used herein the term "mesh count" refers to the number which is the product of the number of wires in a wire mesh screen in both the machine (MD) and cross-machine (CD) directions in a given unit area. For example, a wire mesh screen having 100 wires per inch in the machine direction and 100 wires per inch in the cross machine direction would have a mesh count of 10,000 per square inch. As a result of the interweaving of these wires, raised areas are present on both sides of the mesh screen. The number of raised areas on one side of such a wire mesh screen is generally one-half of the mesh count.

As used herein the term "microarea" refers to an area which has an area of less than about 100,000 square micrometers. The area of the microarea is to be measured by microscopic enlargement.

As used herein the terms "thinned area" or "area thinned" refer to an area in a sheet material having a thickness which is at least about 25 percent less than the thickness of the surrounding sheet material. For example, the thinned area may have a thickness which is at least about 50 percent less than the thickness of the surrounding sheet material. More particularly, the thinned area may have a thickness which is at least about 75 percent less than the surrounding sheet material. Even more particularly, the thinned area may have a thickness which is at least about 90 percent less than the surrounding sheet material. Because the thinning process may not be exactly uniform, the thickness of a thinned area is to be measured at its thinnest point.

As used herein the term "ultrasonic vibrations" refers to vibrations having a frequency of at least about 20,000 cycles per second. The frequency of the ultrasonic vibrations may range from about 20,000 to about 400,000 cycles per second.

As used herein the terms "polymer" or "polymeric" refer to a macromolecule formed by the chemical union of five (5) or more identical combining units called monomers.

As used herein the term "naturally occurring polymeric material" refers to a polymeric material which occurs naturally. The term is also meant to include materials, such as cellophane, which can be regenerated from naturally occurring materials, such as, in the case of cellophane, cellulose. Examples of such naturally occurring polymeric materials include, without limitation, (1) polysaccharides such as starch, cellulose, pectin, seaweed gums (such as agar, etc.), vegetable gums (such as arabic, etc.); (2) polypeptides; (3) hydrocarbons such as rubber and gutta percha (polyisoprene) and (4) regenerated materials such as cellophane or chitosan.

As used herein the terms "metal" or "metallic" refer to an element that forms positive ions when its compounds are in solution and whose oxides form hydroxides rather that acids with water.

As used herein the term "thermoset material" refers to a high polymer that solidifies or "sets" irreversibly when heated. This property is almost invariably associated with a cross-linking reaction of the molecular constituents induced by heat or irradiation. In many cases, it is necessary to add "curing" agents such as organic peroxides or (in the case of natural rubber) sulfur to achieve cross-linking. For example thermoplastic linear polyethylene can be cross-linked to a thermosetting material either by radiation or by chemical reaction. A general discussion of cross-linking can be found at pages 331 to 414 of volume 4 of the Encyclopedia of Polymer Science and Technology, Plastics, Resins, Rubbers, Fibers published by John Wiley & Sons, Inc. and copyrighted in 1966. This document has a Library of Congress Catalog Card No. of 64-22188. Phenolics, alkylds, amino resins, polyesters, epoxides, and silicones are usually considered to be thermosets. The term is also meant to encompass materials where additive-induced cross-linking is possible, e.g. cross-linked natural rubber.

One method for determining whether a material is "cross-linked" and therefore a thermoset material, is to reflux the material in boiling toluene, xylene or another solvent, as appropriate, for forty (40) hours. If a weight percent residue of at least 5 percent remains the material is deemed to be cross-linked. Another procedure for determining whether a material is cross-linked vel non is to reflux 0.4 gram of the material in boiling toluene or another appropriate solvent, for example xylene, for twenty (20) hours. If no insoluble residue (gel) remains the material may not be cross-linked. However, this should be confirmed by the "melt flow" procedure below. If, after twenty (20) hours of refluxing insoluble residue (gel) remains the material is refluxed under the same conditions for another twenty (20) hours. If more than 5 weight percent of the material remains upon conclusion of the second refluxing the material is considered to be cross-linked. Desirably, a least two replicates are utilized. Another method whereby cross-linking vel non and the degree of cross-linking can be determined is by ASTM-D-2765-68 (Reapproved 1978). Yet another method for determining whether a material is cross-linked vel non is to determine the melt flow of the material in accordance with ASTM D 1238-79 at 230° Centigrade while utilizing a 21,600 gram load. Materials having a melt flow of greater than 75 grams per ten minutes shall be deemed to be non-cross-linked. This method should be utilized to confirm the "gel" method described above whenever the remaining insoluble gel content is less than 5% since some cross-linked materials will evidence a residual gel content of less than 5 weight percent.

As used herein the term "thermoplastic material" refers to a high polymer that softens when exposed to heat and returns to its original condition when cooled to room temperature. Natural substances which exhibit this behavior are crude rubber and a number of waxes. Other exemplary thermoplastic materials include, without limitation, polyvinyl chloride, polyesters, nylons, fluorocarbons, linear polyethylene such as linear low density polyethylene, polyurethane prepolymer, polystyrene, polypropylene, polyvinyl alcohol, caprolactams, and cellulosic and acrylic resins.

As used herein the term "hydrosonics" refers to the application of ultrasonic vibrations to a material where the area of such application has had a liquid applied thereto to the extent that the liquid is present in sufficient quantity to generally fill the gap between the tip of the ultrasonic horn and the surface of the material.

OBJECTS OF THE INVENTION

Accordingly, it is a general object of the present invention to provide a process for area thinning thin sheet materials in a generally uniform pattern.

Yet a further object of the present invention is to provide thin sheet materials which have been area thinned is a generally uniform pattern.

Still further objects and the broad scope of applicability of the present invention will become apparent to those of skill in the art from the details given hereinafter. However, it should be understood that the detailed description of the presently preferred embodiments of the present invention is given only by way of illustration because various changes and modifications well within the spirit and scope of the invention will become apparent to those of skill in the art in view of this detailed description.

SUMMARY OF THE INVENTION

In response to the forgoing problems and difficulties encountered by those in the art, we have developed a method for forming thinned areas in a thin sheet material having a thickness of about 10 mils or less. The method includes the steps of: (a) placing the thin sheet material on a pattern anvil having a pattern of raised areas where the height of the raised areas is generally less than the thickness of the thin sheet material; (b) conveying the thin sheet material, while placed on the pattern anvil, through an area where a fluid is applied to the thin sheet material; and (c) subjecting the thin sheet material to ultrasonic vibrations in the area where the fluid is applied to the thin sheet material. As a result of this method the thin sheet material is area thinned in a pattern generally the same as the pattern of raised areas on the pattern anvil.

In some embodiments the fluid may be selected from the group including one or more of water, mineral oil, a chlorinated hydrocarbon, ethylene glycol or a solution of 50 volume percent water and 50 volume percent 2 propanol. For example, the chlorinated hydrocarbon may be selected from the group including 1,1,1 trichloroethane or carbon tetrachloride.

In some embodiments the thin sheet material is area thinned with a thinned area density of at least about 1,000 thinned areas per square inch. For example, the thin sheet material may be area thinned with a thinned area density of at least about 5,000 thinned areas per square inch. More particularly, the thin sheet material may be area thinned, with a thinned area density of at least about 20,000 thinned areas per square inch. Even more particularly, the thin sheet material may be area thinned with a thinned area density of at least about 90,000 thinned areas per square inch. Yet even more particularly, the thin sheet material may be area thinned with a thinned area density of at least about 160,000 thinned areas per square inch.

In some embodiments, the thinned areas are microareas. For example, the area of each of the thinned microareas may generally range from at least about 10 square micrometers to about 100,000 square micrometers. More particularly, the area of each of the thinned microareas generally may range from at least about 10 square micrometers to about 1,000 square micrometers. Even more particularly, the area of each of the thinned microareas may generally range from at least about 10 square micrometers to about 100 square micrometers.

In some embodiments, the pattern anvil may be a mesh screen. In other embodiments the pattern anvil may be a flat plate with raised areas. In even other embodiments, the pattern anvil may be a cylindrical roller with raised areas.

In some embodiments the thin sheet material is area thinned only in selected predesignated areas.

In some embodiments, the thin sheet material is subjected to at least to steps (b) and (c) more than one time.

In some embodiments the height of the raised areas is greater than the thickness of the thin sheet material and the thin sheet material is formed from a material having a resilience such that the thin sheet material is area thinned as opposed to being apertured by the application of hydrosonic energy.

In some embodiments, the mechanism for subjecting the sheet material to ultrasonic vibrations is an ultrasonic horn where the ultrasonic horn has a tip which may be aligned, with respect to the thin sheet material, at an angle of from about 5 degrees to about 15 degrees. For example, the tip of the ultrasonic horn may be aligned, with respect to the thin sheet material, at an angle of from about 7 to about 13 degrees. More particularly, the tip of the ultrasonic horn may be aligned, with respect to the thin sheet material, at an angle of from about 9 to about 11 degrees.

The invention is also directed to a thin sheet material having at least about 1,000 thinned areas per square inch. For example, the thin sheet material may have at least about 5,000 thinned areas per square inch. More particularly, the thinned sheet material may have at least about 20,000 thinned areas per square inch. Even more particularly, the thinned sheet material may have at least about 90,000 thinned areas per square inch. Yet even more particularly, the thinned sheet material may have at least about 160,000 thinned areas per square inch.

In some embodiments, the average thickness of the sheet material may be at least about 0.25 mil. For example, the average thickness of the sheet material may range from about 0.25 mil to about 5 mils. More particularly, the average thickness of the sheet material may range from about 0.25 mil to about 2 mils. Yet even more particularly, the average thickness of the sheet material may range from about 0.5 mil to about 1 mil.

In some embodiments the thinned areas are microareas. For example the area of each of the thinned areas may generally range from at least about 10 square micrometers to about 100,000 square micrometers. More particularly, the area of each of the thinned areas may range from at least about 10 square micrometers to about 10,000 square micrometers. Even more particularly, the area of each of the thinned areas may range from at least about 10 square micrometers to about 5,000 square micrometers. Yet even more particularly, the area of each of the thinned areas may range from at least about 10 square micrometers to about 1,000 square micrometers.

In some embodiments the thinned sheet material is breathable and the water vapor transmission rate of the thinned sheet material is at least about 200 grams per square meter per day. For example, the water vapor transmission rate of the thinned sheet material may be at least at least about 500 grams per square meter per day. More particularly, the water vapor transmission rate of the thinned sheet material may be at least at least about 1,000 grams per square meter per day.

DETAILED DESCRIPTION OF THE INVENTION

Figure 1:
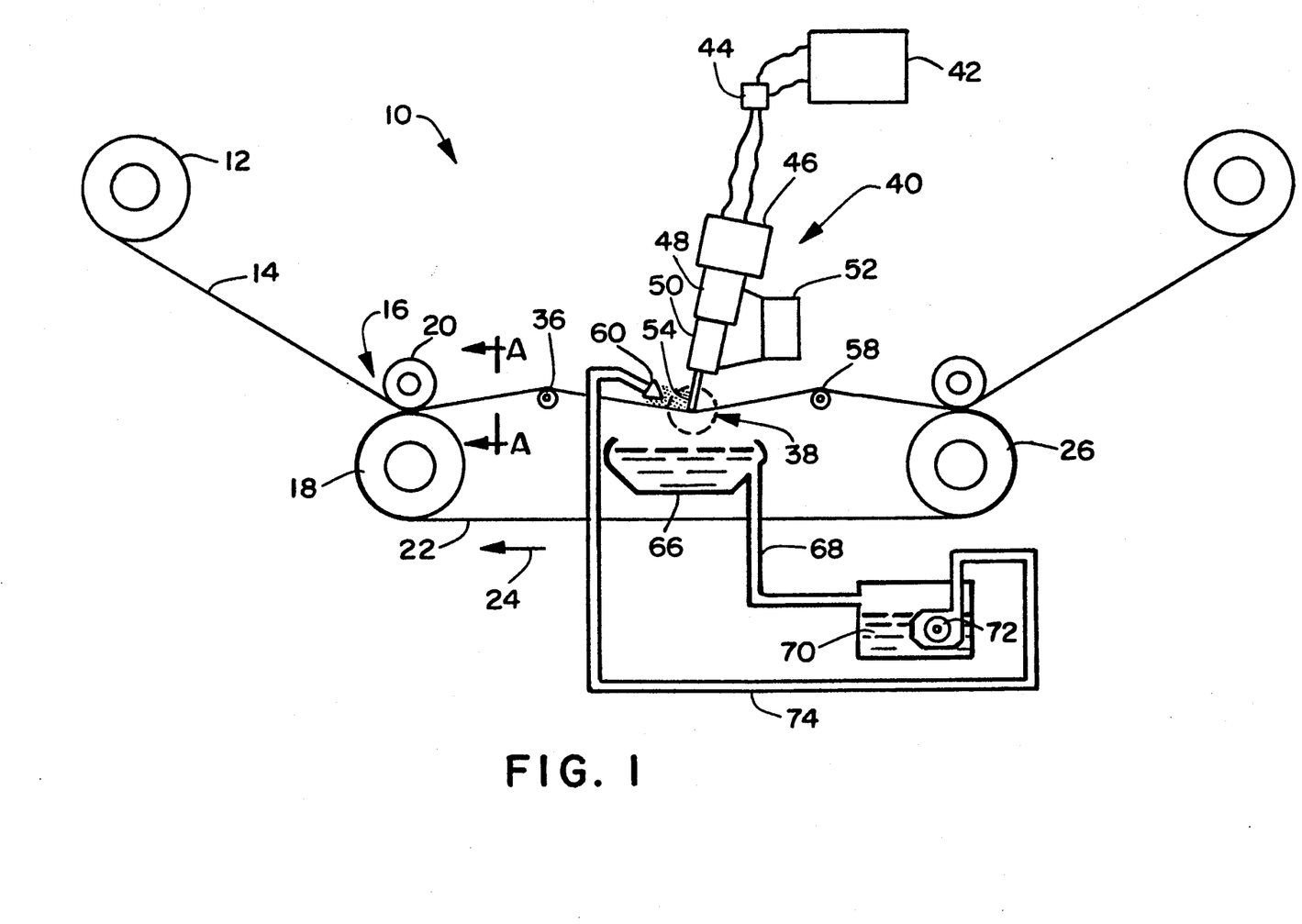
FIG. 1 is a schematic representation of apparatus which may be utilized to apply ultrasonic vibrations to thin sheet materials to thin areas in the thin sheet materials.

Turning now to the Figures where like reference numerals represent like structure and, in particular to FIG. 1 which is a schematic representation of an apparatus which can carry out the method of the present invention, it can be seen that the apparatus is generally represented by the reference numeral 10. In operation, a supply roll 12 of a thin sheet material 14 to be area thinned is provided. As has been previously stated, the term thin sheet material refers to sheet materials which have an average thickness of about ten (10) mils or less. Additionally, generally speaking, the average thickness of the thin sheet material 14 will be at least about 0.25 mil. For example, the average thickness of the thin sheet 14 material may range from about 0.25 mil to about 5 mils. More particularly, the average thickness of the thin sheet material 14 may range from about 0.25 mil to about 2 mils. Even more specifically, the average thickness of the thin sheet material 14 may range from about 0.5 mil to about 1 mil.

The thin sheet material 14 may be formed from a wide variety of materials. For example, the thin sheet material may be formed from a thermoplastic film. The thermoplastic film may be formed from a material selected from the group including one or more polyolefins, polyurethanes, polyesters, A—B—A' block copolymers where A and A' are each a thermoplastic polymer endblock which includes a styrenic moiety and where A may be the same thermoplastic polymer endblock as A', and where B is an elastomeric polymer midblock such as a conjugated diene or a lower alkene or ethylene vinyl acetate copolymer. The polyolefin may be selected from the group including one or more of linear low density polyethylene, polyethylene or polypropylene. The thermoplastic film may be a filled film with the filled film being selected form the group including a polyethylene film filed with starch, titanium dioxide, wax, carbon or calcium carbonate.

Alternatively, the sheet material may be a thermoset film. The thermoset film may be formed from a material selected from the group including of one or more cross-linked polyesters, cross-linked natural rubber or cross-linked dimethyl siloxane.

In other embodiments the sheet material may be a metal. For example, the metal may be selected from the group including aluminum, copper, gold, silver, zinc, lead, iron or platinum.

In even further embodiments the sheet material may be a naturally occurring polymeric material. For example, the naturally occurring polymeric material may be selected from the group including cellophane, cellulose acetate, collagen or carrageenan.

Other appropriate sheet materials will be apparent to those of skill in the art after review of the present disclosure.

The thin sheet material 14 is transported to a first nip 16 formed by a first transport roll 18 and a first nip roller 20 by the action of an endless transport mechanism 22 which moves in the direction indicated by the arrow 24. The transport mechanism 22 is driven by the rotation of the first transport roller 18 in conjunction with a second transport roller 26 which, in turn, are driven by a conventional power source, not shown.

Figure 2:
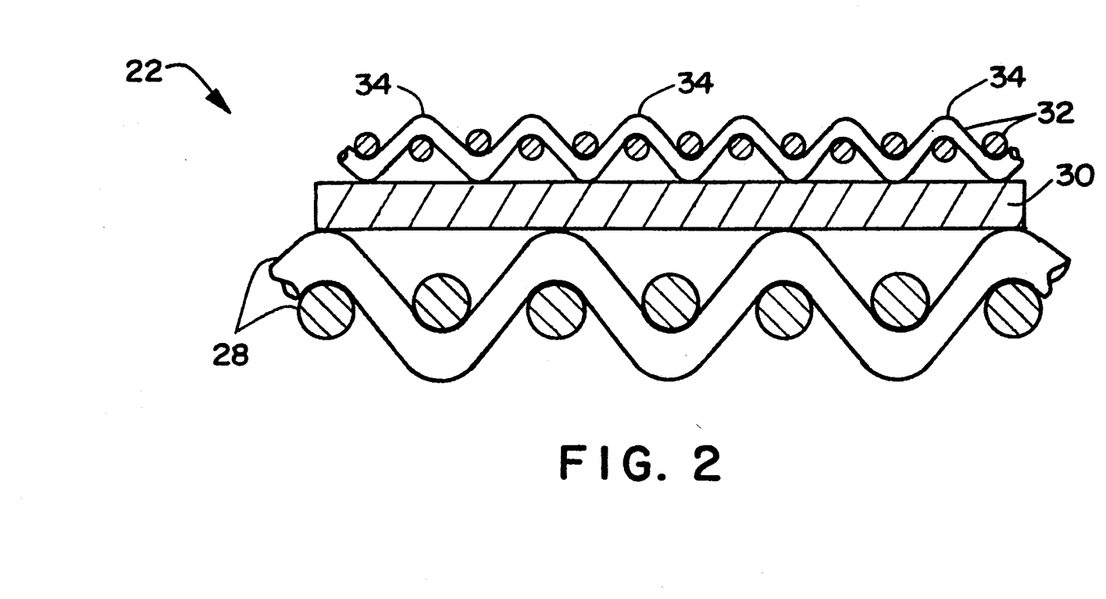
FIG. 2 is a cross sectional view of the transport mechanism for transporting the thin sheet material to the area where it is subjected to ultrasonic vibrations.

FIG. 2 is a cross sectional view of the transport mechanism 22 taken along lines A—A in FIG. 1. FIG. 2 discloses that the transport mechanism 22 includes a heavy duty transport wire mesh screen 28 usually having a mesh count of less than about 400 (i.e. less than about 20 wires per inch by 20 wires per inch mesh screen if machine direction (MD) and cross machine direction (CD) wire count is the same). Heavy duty mesh wire screens of this type may be made from a variety of materials such as, for example, metals, plastics, nylons or polyesters, and are readily available to those in the art. Located above and attached to the transport screen 28 is an endless flat shim plate 30. The shim plate 30 desirably is formed from stainless steel. However, those of skill in the art will readily recognize that other materials may be utilized. Located above and attached to the shim plate 30 is a fine mesh wire pattern screen 32 usually having a mesh count of at least about 2,000 per square inch (i.e. at least a 45 wires per MD inch by 45 wires per CD inch mesh screen if MD and CD wire count is the same). Fine mesh wire screens of this type are readily available to those in the art. The fine mesh wire screen 32 has raised areas or knuckles 34 which perform the function of a pattern anvil as will be discussed later.

From the first nip 16 the thin sheet material 14 is transported by the transport mechanism 22 over a tension roll 36 to an are 38 (defined in FIG. 1 by the dotted lined circle) where the thin sheet material 14 is subjected to ultrasonic vibrations.

The assembly for subjecting the thin sheet material 14 to the ultrasonic vibrations is conventional and is generally designated at 40. The assembly 40 includes a power supply 42 which, through a power control 44, supplies power to a piezoelectric transducer 46. As is well known in the art, the piezoelectric transducer 46 transforms electrical energy into mechanical movement as a result of the transducer's vibrating in response to an input of electrical energy. The vibrations created by the piezoelectric transducer 46 are transferred, in conventional manner, to a mechanical movement booster or amplifier 48. As is well known in the art, the mechanical movement booster 48 may be designed to increase the amplitude of the vibrations (mechanical movement) by a known factor depending upon the configuration of the booster 48. In further conventional manner, the mechanical movement (vibrational energy) is transferred from the mechanical movement booster 48 to a conventional knife edge ultrasonic horn 50. It should be realized that other types of ultrasonic horns 50 could be utilized. For example, a rotary type ultrasonic horn could be used. The ultrasonic horn 50 may be designed to effect yet another boost or increase in the amplitude of the mechanical movement (vibrations) which is to be applied to the thin sheet material 14. Lastly, the assembly includes an actuator 52 which includes a pneumatic cylinder, not shown. The actuator 52 provides a mechanism for raising and lowering the assembly 40 so that the tip 54 of the ultrasonic horn 50 can apply tension to the transport mechanism 22 upon the assembly 40 being lowered. It has been found that it is necessary to have some degree of tension applied to the transport mechanism 22 upon the lowering of the assembly for proper application of vibrational energy to the thin sheet material 14 to form thinned areas in the thin sheet material 14. One desirable aspect of this tensioned arrangement is that the need to design a finely toleranced gap between the tip 54 of the horn 50 and the raised areas or knuckles 34 of the fine mesh wire screen 32 is not necessary.

Figure 3:
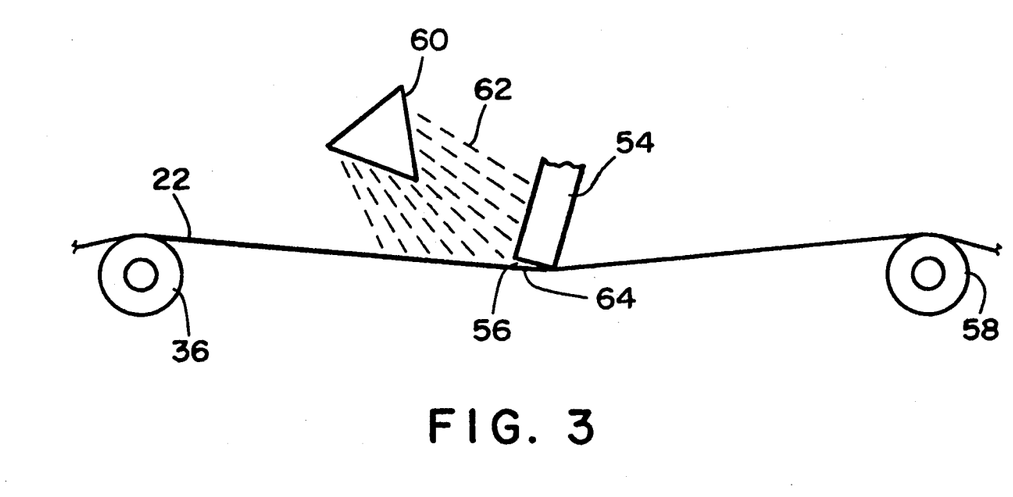
FIG. 3 is a detailed view of the area where the thin sheet material is subjected to ultrasonic vibrations. The area is designated by the dotted circle in FIG. 1.

FIG. 3 is a schematic representation of the area 38 where the ultrasonic vibrations are applied to the thin sheet material 14. As can be seen in FIG. 3, the transport mechanism 22 forms an angle 56 with the tip 54 of the ultrasonic horn 50. While some area thinning will occur if the angle 56 is as great as 45 degrees, it has been found that it is desirable for the angle 56 to range from about 5 degrees to about 15 degrees. For example, the angle 56 may range from about 7 to about 13 degrees. More particularly, the angle 56 may range from about 9 to about 11 degrees.

FIG. 3 also illustrates that the transport mechanism 22 is supported from below by the first tension roll 36 and a second tension roll 58. Positioned somewhat prior to the tip 54 of the ultrasonic horn 50 is a spray nozzle 60 which is configured to apply a fluid 62 to the surface of the thin sheet material 14 just prior to the sheet material's 14 being subjected to ultrasonic vibrations by the tip 54 of the ultrasonic horn 50. The fluid 62 desirably may be selected from the group including one or more of water, mineral oil, a chlorinated hydrocarbon, ethylene glycol or a solution of 50 volume percent water and 50 volume percent 2 propanol. For example, in some embodiments the chlorinated hydrocarbon may be selected from the group including 1,1,1 trichloroethane or carbon tetrachloride. It should be noted that the wedge-shaped area 64 formed by the tip 54 of the ultrasonic horn 50 and the transport mechanism 22 should be subjected to a sufficient amount of the fluid 62 for the fluid 62 to act as both a heat sink and a coupling agent for the most desirable results. Positioned below the transport mechanism 22 in the area where the tip 54 of the ultrasonic horn 50 is located is a fluid collection tank 66. (See FIG. 1.) The fluid collection tank 66 serves to collect fluid 62 which has been applied to the surface of the thin sheet material 14 and which has been driven over the edges of the transport mechanism 22 by the action of the vibrations of the tip 54 of the ultrasonic horn 50. Fluid 62 which is collected in the collection tank 66 is transported by tubing 68 to a fluid holding tank 70.

FIG. 1 illustrates that the fluid holding tank 70 contains a pump 72 which, by way of additional tubing 74, supplies the fluid 62 to the fluid spray nozzle 60. Accordingly, the fluid 62 may be re-cycled for a considerable period of time.

While the mechanism of action may not be fully understood and the present application should not be bound to any particular theory or mechanism of action, it is believed that the presence of the fluid 62 in the wedge-shaped area 64 during operation of the ultrasonic horn 50 accomplishes two separate and distinct functions. First, the presence of the fluid 62 allows the fluid 62 to act as a heat sink which allows the ultrasonic vibrations to be applied to the thin sheet material 14 without the thin sheet material 14 being altered or destroyed as by melting. Secondly, the presence of the fluid 62 in the wedge-shaped area 64 allows the fluid 62 to act as a coupling agent in the application of the vibrations from the ultrasonic horn 50 to the thin sheet material 14.

It has been discovered that the action of the ultrasonic horn 50 on the thin sheet material 14 thins areas in the thin sheet material 14 in spite of the fact that there are no fibers to re-arrange as was the case in Mitchell et al.. The thinned areas are punched into the thin sheet material 14 in the pattern of the raised areas or knuckles 34 of the fine mesh wire pattern screen 32. Generally, the number of thinned areas produced will be equal to the number of raised areas or knuckles 34 on the upper surface of the fine mesh wire screen 32. That is, the number of thinned areas will generally be one-half the mesh count of a given area of pattern screen 32. For example, if the pattern screen 32 is 100 wires per inch MD by 100 wires per inch CD, the total number of knuckles or raised areas 34 on one side of the pattern wire per square inch 32 will be 100 times 100 divided by 2. This equals 5,000 thinned areas per square inch. For a 200 wires per inch MD by 200 wires per inch CD pattern screen 32 the calculation yields 20,000 thinned areas per square inch. Depending somewhat on the thickness of the thin sheet material 14, at a mesh count of about 90,000 (300 wires per inch MD by 300 wires per inch CD) the wires are so thin as to allow the knuckles 34 on both sides to area thin the thin sheet material 14 if sufficient force is applied. Thus, a 300 wires per inch MD by 300 wires per inch CD mesh screen yields 90,000 thinned areas per square inch; for a 400 wires per inch MD by 400 wires per inch CD mesh—160,000 thinned areas per square inch. Of course the MD and CD wire count of the wire mesh screen does not have to be the same.

Also as a result of the area thinning process the edge length of the thin sheet material may be increased by at least about 100 percent as compared to the sheet's edge length prior to area thinning. For example, the edge length of the thin sheet material may be increased by at least about 500 percent as compared to the sheet's edge length prior to area thinning. More particularly, the edge length of the thin sheet material may be increased by at least about 1,500 percent as compared to the sheet's edge length prior to area thinning. Even more particularly, the edge length of the thin sheet material may be increased by at least about 3,000 percent as compared to the sheet's edge length prior to area thinning.

It should also be noted that the number of thinned areas formed may also vary with the number of ultrasonic vibrations to which the thin sheet material 14 is subjected per unit area for a given period of time. This factor may be varied in a number of ways. For example, the number and size of the thinned areas will vary somewhat with the line speed of the thin sheet material 14 as it passes underneath the tip 54 of the ultrasonic horn 50. Generally speaking, as line speed increases, first the size and depth of the thinned areas decreases and then the number of thinned areas decreases. As the number of thinned areas decreases the less the pattern of thinned areas resembles the pattern of raised areas 34 on the pattern screen 32. The range of line speeds that usually yields thinned areas varies with the material utilized to form the thin sheet material 14 and the material used as the fluid 62. For polyethylene film having a thickness of about 1 mil, typical line speeds which are believed to yield thinned areas for a wide variety of fluids range from about 14 to about 28 feet per minute. If water is used as the fluid with such polyethylene film, typical line speeds which are believed to yield thinned areas range from about 14 to about 28 feet per minute. For cellophane having a thickness of about 0.8 mil, typical line speeds which are believed to yield thinned areas for a wide variety of fluids range from about 12 to about 18 feet per minute. If water is used as the fluid with cellophane, typical line speeds which usually yield thinned areas range from about 12 to about 18 feet per minute.

It should be understood that one limitation on the present process is the degree of elasticity of the thin sheet material 14. If the sheet material is formed from a highly elastic material it may be very difficult, if not impossible, to area thin the material. This is due to the fact that, due to extreme resilience, the material will return to generally its original shape after being transiently thinned. Thus, the thinned areas are initially formed but soon disappear due to the memory of the highly elastic sheet material.

It is believed that, to some extent, the variations in the number of thinned areas formed and the size of the thinned areas occurs due to the minute variations in the height of the raised areas or knuckles 34 of the fine mesh pattern screen 32. It should be noted that the fine mesh pattern screens used to date have been obtained from conventional everyday sources such as a hardware store. It is also believed that if a pattern screen 32 could be created where all of the raised areas 34 of the screen 32 were of exactly the same height these variations would only occur in uniform fashion with variations of line speed.

As was stated above, the area or size of each of the thinned areas formed will also vary with the parameters discussed above. The area of the thinned areas will also vary with the area of the raised areas of the pattern anvil such as the knuckles 34 on the fine mesh wire screen 32. It is believed that the type of material used in forming the thin sheet material 14 will also vary the area of the thinned areas formed if all other parameters are maintained the same. For example, the softer the thin sheet material 14, the easier it is to push the thin sheet material 14 through the raised areas of the fine mesh pattern screen 32. Because the raised areas (knuckles) on the fine mesh screen are generally pyramidal in shape, the deeper the raised area penetrates the thin sheet material 14, the larger the and thinner the thinned area. In such situations the shape of the thinned area will conform generally to the pyramidal shape of the raised area of the fine mesh screen and the thinned area will be generally pyramidally shaped, in the z direction. As has been previously stated, the area of the thinned area can be approximately calculated by microscopic enlargement. Usually the height of the raised areas must be less than the thickness of the thin sheet material 14 for thinned areas to be formed. However, in some situations, when the thin sheet material 14 is formed from a very resilient material, the height of the raised areas may be greater than the thickness of the thin sheet material 14 due to the fact that the thin sheet material will stretch and thin but not aperture.

In some embodiments it may be necessary to subject the thin sheet material 14 to multiple passes through the apparatus 10 in order to thin areas in the thin sheet material 14 to the degree desired. In such situations the thin sheet material 14 will initially only be thinned to a slight degree in the pattern of the pattern anvil's raised areas. However, two or more passes through the apparatus 10, with the thin sheet material 14 being aligned in the same configuration with respect to the pattern anvil will yield areas thinned to the degree desired. Essentially what is happening in these situations is that the thin sheet material 14 is repeatedly thinned by repeated application of ultrasonic vibrational force until such time as areas which are thinned to the desired degree are formed. Care should be taken that the areas are not apertured by repeated application of hydrosonic vibrations.

Another feature of the present invention is the fact that the thinned areas can be formed in a predesignated area or areas of the thin sheet material 14. This can be accomplished in a number of ways. For example, the thin sheet material 14 may be subjected to ultrasonic vibrations only at certain areas of the sheet material, thus, area thinning would occur only in those areas. Alternatively, the entire thin sheet material could be subjected to ultrasonic vibrations with the pattern anvil having raised areas only at certain locations and otherwise being flat. Accordingly, the thin sheet material 14 would have thinned areas only in those areas which corresponded to areas on the pattern anvil having raised areas.

It should also be noted that some limitation exists in the number of thinned areas which can be formed in a given thin sheet material 14 on a single application of vibrational energy, i.e. a single pass through the apparatus if a wire mesh screen is used as the pattern anvil. This follows from the fact that the height of the raised areas must be sufficient to effect some thinning of the thin sheet material 14 in conjunction with the fact that, generally as the mesh count increases the height of the raised areas or knuckles decreases. In such situations, if the number of thinned areas desired per unit area is greater than the number which can be formed in one pass through the apparatus, multiple passes are necessary with the alignment of the thin sheet material 14 with respect to the raised ares being altered or shifted slightly on each pass.

In some embodiments the areas may be micro areas. Generally speaking the area of each of the thinned microareas is usually greater than about ten square micrometers. That is the area of each of the thinned microareas may range from at least about 10 square micrometers to about 100,000 square micrometers. For example, the area of each of the formed thinned microareas may generally range from at least about 10 square micrometers to about 10,000 square micrometers. More particularly, the area of each of the thinned microareas formed may generally range from at least about 10 square micrometers to about 1,000 square micrometers. Even more particularly, the area of each of the thinned microareas formed may generally range from at least about 10 square micrometers to about 100 square micrometers.

A number of important observations about the process may now be made. For example, it should be understood that the presence of the fluid 62 is highly important to the present inventive process which uses the fluid as a coupling agent. Because a coupling agent is present, the thinned areas are punched into the thin sheet material 14 as opposed to being formed by melting. The importance of the fluid 62 is further exemplified by the fact that the process has been attempted without the use of the fluid 62 and was not generally successful. Additionally, the presence of the shim plate 30 or its equivalent is necessary in order to provide an anvil mechanism against which the thin sheet material 14 may be worked, that is thinned, by the action of the tip 54 of the ultrasonic horn 50. Because the vibrating tip 54 of the ultrasonic horn 50 is acting in a hammer and anvil manner when operated in conjunction with the heavy duty wire mesh screen 28/shim plate 30/fine wire mesh 32 combination, it should be readily recognized that a certain degree of tension must be placed upon the transport mechanism 22 by the downward displacement of the ultrasonic horn 50. If there is little or no tension placed upon the transport mechanism 22, the shim plate 30 cannot preform its function as an anvil and area thinning generally does not occur. Because both the shim plate 30 and the fine mesh pattern wire 32 form the resistance that the ultrasonic horn 50 works against, they are collectively referred herein as a pattern anvil combination. It should be easily recognized by those in the art that the function of the pattern anvil can be accomplished by other arrangements than the heavy duty wire mesh screen 28/shim plate 30/fine mesh screen 32 combination. For example, the pattern anvil could be a flat plate with raised portions acting to direct the area thinning force of the ultrasonic horn 50. Alternatively, the pattern anvil could be a cylindrical roller having raised areas. If the pattern anvil is a cylindrical roller with raised areas, it is desirable for the pattern anvil to be wrapped or coated with or made from a resilient material. Where the pattern anvil is a mesh screen the resiliency is provided by the fact that the screen is unsupported directly below the point of application of ultrasonic vibrations to the mesh screen.

Depending upon the material used to form the sheet material, the degree of thinning of each thinned area and the number of thinned areas per square inch of the sheet material, the strength of the sheet material will be degraded upon being thinned. The degree of degradation is evidenced by hydrohead testing of the material prior to and after thinning. Of course, the hydrohead tests the height of a column of water that the material can support before failure.

The invention will now be discussed with regard to specific examples which will aid those of skill in the art in a full and complete understanding thereof.

EXAMPLE I

A sheet of 1 mil thick polyethylene film was obtained from the McMaster Carr Corporation of Atlanta, Ga. and was cut into a length of about 11 inches and a width of about 8.5 inches. The sample was subjected to hydrosonic treatment in accordance with the present invention.

A model 1120 power supply obtained from the Branson Company of Danbury, Conn., was utilized. This power supply, which has the capacity to deliver 1,300 watts of electrical energy, was used to convert 115 volt, 60 cycle electrical energy to 20 kilohertz alternating current. A Branson type J4 power level control, which has the ability to regulate the ultimate output of the model 1120 power supply from 0 to 100%, was connected to the model 1120 power supply. In this example, the power level control was set at 100%. The actual amount of power consumed was indicated by a Branson model A410A wattmeter. This amount was about 900 watts.

The output of the power supply was fed to a model 402 piezoelectric ultrasonic transducer obtained from the Branson Company. The transducer converts the electrical energy to mechanical movement. At 100% power the amount of mechanical movement of the transducer is about 0.8 micrometers.

The piezoelectric transducer was connected to a mechanical movement booster section obtained from the Branson Company. The booster is a solid titanium shaft with a length equal to one-half wave length of the 20 kilohertz resonant frequency. Boosters can be machined so that the amount of mechanical movement at their output end is increased or decreased as compared to the amount of movement of the transducer. In this example the booster increased the amount of movement and has a gain ratio of about 1:2.5. That is, the amount of mechanical movement at the output end of the booster is about 2.5 times the amount of movement of the transducer.

The output end of the booster was connected to an ultrasonic horn obtained from the Branson Company. The horn in this example is made of titanium with a working face of about 9 inches by about ½ inch. The leading and trailing edges of the working face of the horn are each curved on a radius of about ⅛ inch. The horn step area is exponential in shape and yields about a two-fold increase in the mechanical movement of the booster. That is, the horn step area has about a 1:2 gain ratio. The combined increase, by the booster and the horn step area, in the original mechanical movement created by the transducer yields a mechanical movement of about 4.0 micrometers.

The forming table arrangement included a small forming table which was utilized to transport and support the sheet of polyethylene to be area thinned. The forming table included two 2-inch diameter idler rollers which were spaced about 12 inches apart on the surface of the forming table. A transport mesh belt encircles the two idler rollers so that a continuous conveying or transport surface is created. The transport mesh belt is a square weave 20×20 mesh web of 0.020 inch diameter plastic filaments. The belt is about 10 inches wide and is raised above the surface of the forming table.

The transducer/booster/horn assembly, hereinafter the assembly, is secured in a Branson series 400 actuator. When power is switched on to the transducer, the actuator, by means of a pneumatic cylinder with a piston area of about 4.4 square inches, lowers the assembly so that the output end of the horn contacts the sheet of polyethylene which is to be area thinned. The actuator also raises the assembly so that the output end of the horn is removed from contact with the sheet of polyethylene film when the power is switched off.

The assembly is positioned so that the output end of the horn is adapted so that it may be lowered to contact the transport mesh belt between the two idler rollers. An 8-inch wide 0.01-inch thick stainless steel shim stock having a length of about 60 inches was placed on the plastic mesh transport belt to provide a firm support for a pattern screen which is placed on top of the stainless steel shim. In this example the pattern screen is a 60 by 60 mesh wire size weave stainless steel screen. The sheet of polyethylene film which was to be area thinned was then fastened onto the pattern wire using masking tape.

The forming table arrangement also included a fluid circulating system. The circulating system includes a fluid reservoir tank, a fluid circulating pump which may conveniently be located within the tank, associated tubing for transporting the fluid from the tank to a slotted boom which is designed to direct a curtain of fluid into the juncture of the output end of the horn and sheet of polyethylene which is to be area thinned.

In operation, the assembly was positioned so that the output end of the horn was at an angle of from about 10 to 15 degrees to the sheet of polyethylene to be area thinned. Accordingly, a wedge shaped chamber was formed between the output end of the horn and the sheet of polyethylene to be area thinned. It is into this wedge shaped chamber that the fluid, in this example water at room temperature, is directed by the slotted boom.

It should be noted that the actuator was positioned at a height to insure that, when the assembly is lowered, the downward movement of the output end of the horn is stopped by the tension of the transport mesh before the actuator reaches the limit of its stroke. In this example, actuating pressure was adjusted to 4 pounds per square inch as read on a pressure gauge which is attached to the pneumatic cylinder of the actuator. This adjustment results in a total downward force of 17.6 pounds. (4 psi times 4.4 square inches of piston area equals 17.6 pounds of force.)

The sequence of operation was (1) the fluid pump was switched on and the area where the output end of the horn was to contact the sheet of polyethylene film was flooded with water; (2) the transport mesh conveyor system was switched on and the polyethylene started moving at 20 feet per minute; and (3) power to the assembly was supplied and the assembly was lowered so that the output end of the horn contacted the sheet of polyethylene film while the sheet continued to pass under the output end of the horn until the end of the sample was reached. The reading on the A410A wattmeter during the process is an indication of the energy required to maintain maximum mechanical movement at the output end of the horn while working against the combined mass of the fluid, the sheet of polyethylene, the pattern wire, the shim stock, and the transport wire.

This example yielded an area thinned polyethylene film having a maximum thinned area density of about 1,800 thinned areas per square inch with each thinned area having an area of about 3,000 square micrometers. The thickness of each thinned area was about 3 micrometers.

The water vapor transmission rate of this material after thinning was measured as being about 300 grams per square meter per day. Prior to thinning, the water vapor transmission rate of this material was measured as being about zero (0). Accordingly, the thinning process turned a non-breathable material into a breathable material. The hydrohead of this material prior to thinning was measured as being in excess of 137 centimeters of water. After thinning in accordance with Example I, the hydrohead was measured as being 103. Thus, the thinned sheet material retained a good portion of its strength after thinning.

Figure 4:
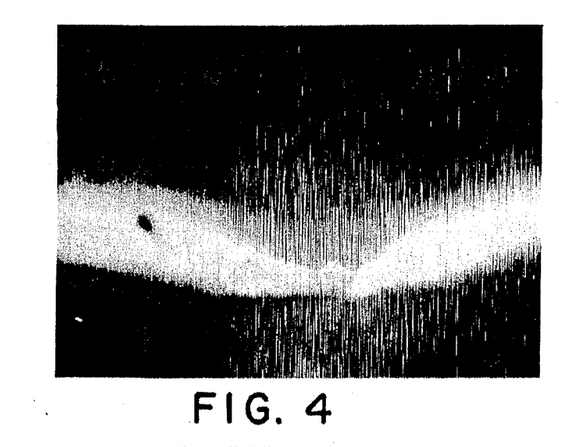
FIG. 4 is a cross sectional photomicrograph of a 1 mil thick sheet of polyethylene film which has been area thinned in accordance with the present invention.
Figure 5:
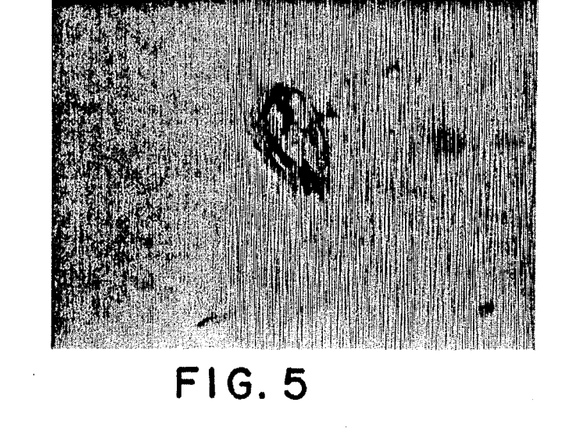
FIG. 5 is a plan view of a thinned area of the film of FIG. 4.
Figure 6:
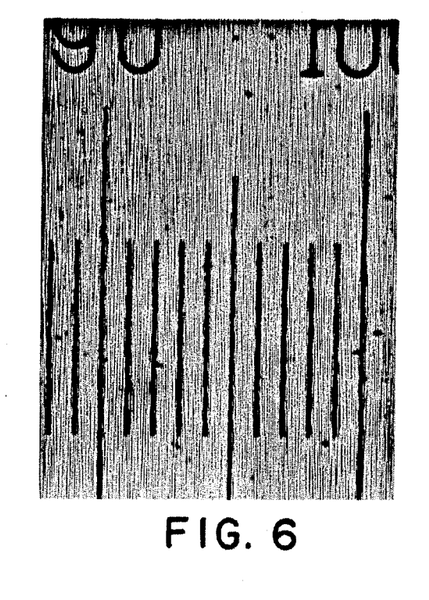
FIG. 6 is a scale for use with FIGS. 4 and 5 where each unit represents ten (10) microns (micrometers).

FIGS. 4 and 5 are two photomicrographs of the thin sheet material which is area thinned in accordance with Example I. FIG. 4 is a cross-section of the sheet through a thinned area and FIG. 5 is a top view of a thinned area. FIG. 6 is a scale for use with FIGS. 4 and 5 where each unit represents ten (10) microns (micrometers).

EXAMPLE II

The process of example I was repeated with the exception that a sheet of a 1.4 mil thick filled film which is loaded with 50-60%, by weight (40% by volume)

calcium carbonate particles obtained from the DuPont Chemical Company of Canada under the trade designation "Evlon" was utilized as the thin sheet material. The line speed of was about 15 feet per minute as compared to the 20 feet per minute utilized in example I. The actual amount of power consumed was indicated by the Branson model A410A wattmeter as about 800 watts.

This example yielded a microarea thinned sheet having a maximum density of about 1,800 thinned areas per square inch with each thinned area having an area of about 6,000 square micrometers. The thickness of each thinned area was about 4 micrometers.

The water vapor transmission rate of this material after thinning was measured several times will variable results. That is, after thinning, the water vapor transmission rate was measured as being about 468, 842 and 124 grams per square meter per day. Prior to thinning, the water vapor transmission rate of this material was measured as being about 93.8 grams per square meter per day. Accordingly, the thinning process significantly improved the breathability of this material.

The hydrohead of this material prior to thinning was measured as being in excess of 137 centimeters of water. After thinning in accordance with Example II, the hydrohead was measured as being 91. Thus, the thinned sheet material retained a good portion of its strength after thinning.

Figure 7:
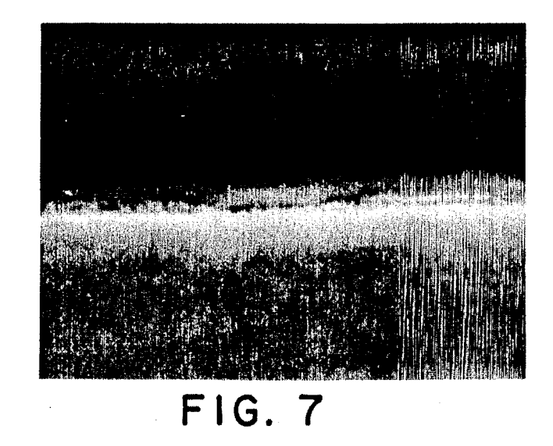
FIG. 7 is a cross sectional photomicrograph of a 1.4 mil thick sheet of Dupont film sold under the trade designation "Evlon" which has been area thinned in accordance with the present invention.
Figure 8:
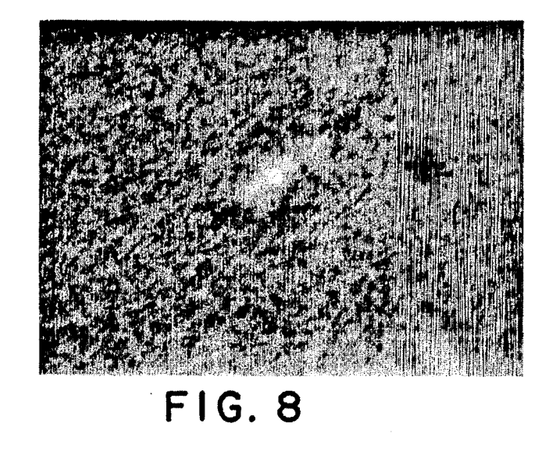
FIG. 8 is a plan view of a thinned area of the film of FIG. 7.
Figure 9:
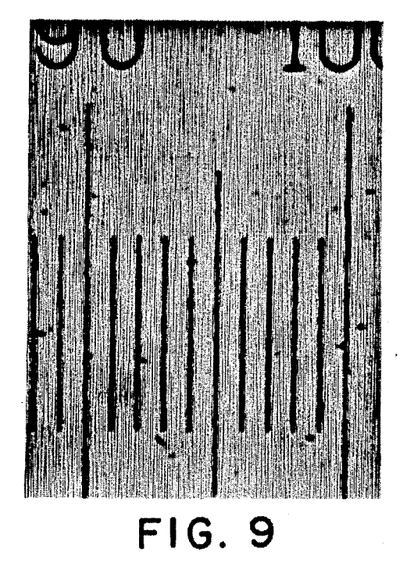
FIG. 9 is a scale for use with FIGS. 7 and 8 where each unit represents ten (10) microns (micrometers).

FIGS. 7 and 8 are two photomicrographs of the thin sheet material which is area thinned in accordance with Example II. FIG. 7 is a cross-section of the sheet through a thinned area and FIG. 8 is a top view of a thinned area. FIG. 9 is a scale for use with FIGS. 7 and 8 where each unit represents ten (10) microns (micrometers).

EXAMPLE III

The process of example I was repeated with the exception that a sheet of a 0.8 mil thick sheet of cellophane obtained under the trade name "Flexel V-58" was utilized as the thin sheet material. The line speed of was about 4.5 feet per minute as compared to the 20 feet per minute utilized in example I. The actual amount of power consumed was indicated by the Branson model A410A wattmeter as about 800 watts. A 250 by 250 stainless steel fine mesh screen was used.

This example yielded a microarea thinned cellophane sheet having a maximum density of about 62,500 thinned areas per square inch with each thinned area having an area of about 650 square micrometers. The thickness of each thinned area was about 2 micrometers.

The water vapor transmission rate of this material after thinning was measured as being about 200 grams per square meter per day. Prior to thinning, the water vapor transmission rate of this material was measured as being about 0.0 grams per square meter per day. Accordingly, the thinning process significantly improved the breathability of this material.

The hydrohead of this material prior to thinning was measured as being in excess of 137 centimeters of water. After thinning in accordance with Example III, the hydrohead was measured as being 137. Thus, no loss of strength was detected by our equipment.

Figure 10:
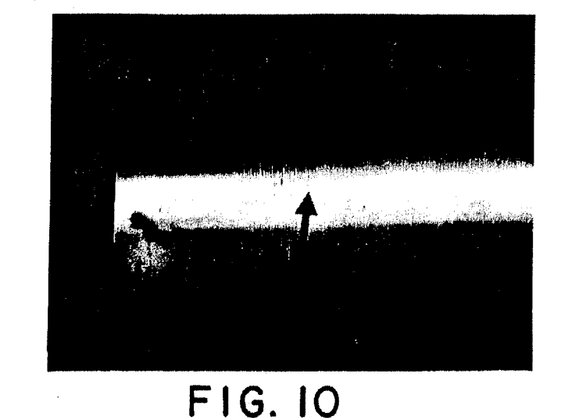
FIG. 10 is a cross sectional photomicrograph of a 0.8 mil thick sheet of cellophane sold under the trade designation Flexel V-58 which has been area thinned in accordance with the present invention.
Figure 11:
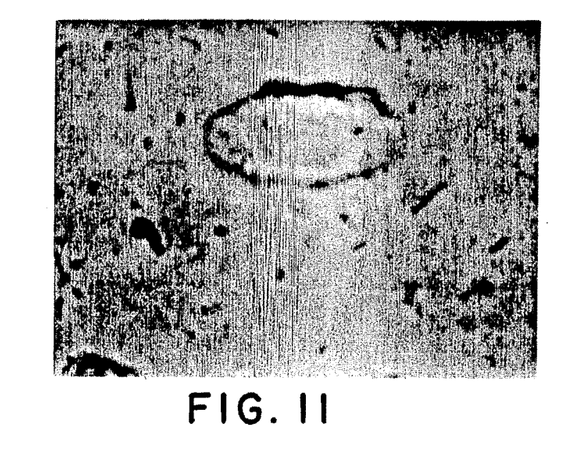
FIG. 11 is a plan view of a thinned area of the film of FIG. 10.
Figure 12:
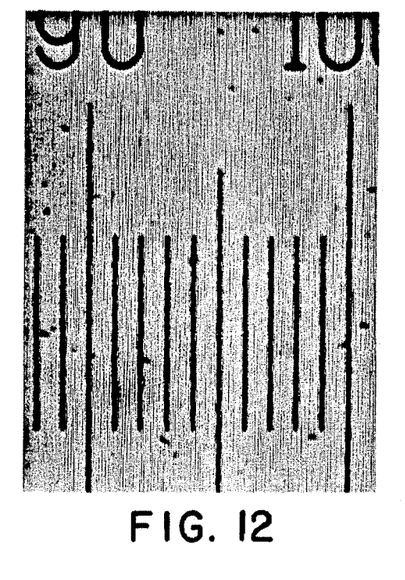
FIG. 12 is a scale for use with FIGS. 10 and 11 where each unit represents ten (10) microns (micrometers).

FIGS. 10 and 11 are two photomicrographs of the thin sheet material which is area thinned in accordance with Example III. FIG. 10 is a cross-section of the sheet through a thinned area and FIG. 11 is a top view of a thinned area. Due to the presence of significant background light, it is difficult to discern the thinned area on cross-section. Accordingly, an arrow has been added to the photomicrograph to better demonstrate the degree of thinning. FIG. 12 is a scale for use with FIGS. 10 and 11 where each unit represents ten (10) microns (micrometers).

The uses to which the area thinned thin sheet material of the present invention may be put are numerous. Let it suffice to state that the increased breathability of the sheet materials makes them well suited for barrier fabric applications.

It is to be understood that variations and modifications of the present invention may be made without departing from the scope of the invention. For example, in some embodiments the use of multiple ultrasonic horns aligned abreast or sequentially may be desirable. It is also to be understood that the scope of the present invention is not to be interpreted as limited to the specific embodiments disclosed herein, but only in accordance with the appended claims when read in light of the foregoing disclosure.

What is claimed is:

1. A sheet material, having an average thickness of less than about ten mils, with at least a portion thereof having a generally uniform pattern of at least 1,000 thinned areas per square inch, wherein each of the thinned areas has a thickness which is at least 25 percent less than the thickness of the surrounding sheet material.

2. The sheet material of claim 1, having at least 5,000 thinned areas per square inch.

3. The sheet material of claim 1, having at least 20,000 thinned areas per square inch.

4. The sheet material of claim 1, having at least 90,000 thinned areas per square inch.

5. The sheet material of claim 1, wherein the average thickness of the sheet material is at least 0.25 mil.

6. The sheet material of claim 1, wherein the average thickness of the sheet material is from about 0.25 mil to about 5 mils.

7. The sheet material of claim 1, wherein the average thickness of the sheet material is from about 0.25 mil to about 2 mils.

8. The sheet material of claim 1, wherein the average thickness of the sheet material is from about 0.5 mil to about 1 mils.

9. The sheet material of claim 1, wherein the areas are microareas.

10. The sheet material of claim 9, wherein the area of each of the microareas generally ranges from at least 10 square micrometers to about 100,000 square micrometers.

11. The sheet material of claim 9, wherein the area of each of the microareas generally ranges from at least 10 square micrometers to about 10,000 square micrometers.

12. The sheet material of claim 9, wherein the area of each of the microareas generally ranges from at least 10 square micrometers to about 5,000 square micrometers.

13. The sheet material of claim 9, wherein the area of each of the microareas generally ranges from at least 10 square micrometers to about 1,000 square micrometers.

14. The sheet material of claim 1, wherein the area thinning is confined to a predesignated area of areas of the thin sheet material.

15. The sheet material of claim 1, wherein the sheet material is a water insoluble material and the water vapor transmission rate of the sheet material is at least 200 grams per square meter per day.

16. The sheet material of claim 1, wherein the sheet material is a water insoluble material and the water vapor transmission rate of the sheet material is at least 500 grams per square meter per day.

17. The sheet material of claim 1, wherein the sheet material is a water insoluble material and the water vapor transmission rate of the sheet material is at least 1,000 grams per square meter per day.

18. The sheet material of claim 1, having at least 160,000 thinned areas per square inch.

19. The sheet material of claim 1, wherein the thinned areas are microareas.

20. The sheet material of claim 1, wherein the area of each of the thinned microareas generally ranges from at least about 10 square micrometers to about 100,000 square micrometers.

21. The sheet material of claim 1, wherein the area of each of the thinned microareas generally ranges from at least about 10 square micrometers to about 1,000 square micrometers.

22. The sheet material of claim 1, wherein the area of each of the thinned microareas generally ranges from at least about 10 square micrometers to about 100 square micrometers.

23. A sheet material, having an average thickness of less than about ten mils, with at least a portion thereof having a generally uniform pattern of at least 1,000 thinned areas per square inch, wherein each of the thinned areas has a thickness which is at least 50 percent less than the thickness of the surrounding sheet material.

24. The sheet material of claim 23, wherein the area of each of the thinned microareas generally ranges from at least about 10 square micrometers to about 100,000 square micrometers.

25. The sheet material of claim 23, wherein the area of each of the thinned microareas generally ranges from at least about 10 square micrometers to about 1,000 square micrometers.

26. The sheet material of claim 23, wherein the area of each of the thinned microareas generally ranges from at least about 10 square micrometers to about 100 square micrometers.

27. The sheet material of claim 23, having a generally uniform pattern of at least 5,000 thinned areas per square inch.

28. The sheet material of claim 23, having a generally uniform pattern of at least 20,000 thinned areas per square inch.

29. The sheet material of claim 23, having a generally uniform pattern of at least 90,000 thinned areas per square inch.

30. The sheet material of claim 23, having a generally uniform pattern of at least 160,000 thinned areas per square inch.

31. The sheet material of claim 23, wherein the sheet material is a water insoluble material and the water vapor transmission rate of the sheet material is at least 200 grams per square meter per day.

32. The sheet material of claim 23, wherein the sheet material is a water insoluble material and the water vapor transmission rate of the sheet material is at least 500 grams per square meter per day.

33. The sheet material of claim 23, wherein the sheet material is a water insoluble material and the water vapor transmission rate of the sheet material is at least 1,000 grams per square meter per day.

34. A sheet material, having an average thickness of less than about ten mils, with at least a portion thereof having a generally uniform pattern of at least 1,000 thinned areas per square inch, wherein each of the thinned areas has a thickness which is at least 75 percent less than the thickness of the surrounding sheet material.

35. The thin sheet material of claim 34, wherein the area of each of the thinned microareas generally ranges from at least about 10 square micrometers to about 100,000 square micrometers.

36. The thin sheet material of claim 34, wherein the area of each of the thinned microareas generally ranges from at least about 10 square micrometers to about 1,000 square micrometers.

37. The thin sheet material of claim 34, wherein the area of each of the thinned microareas generally ranges from at least about 10 square micrometers to about 100 square micrometers.

38. The thin sheet material of claim 34, having a generally uniform pattern of at least 5,000 thinned areas per square inch.

39. The thin sheet material of claim 34, having a generally uniform pattern of at least 20,000 thinned areas per square inch.

40. The thin sheet material of claim 34, having a generally uniform pattern of at least 90,000 thinned areas per square inch.

41. The thin sheet material of claim 34, having a generally uniform pattern of at least 160,000 thinned areas per square inch.

42. The sheet material of claim 34, wherein the sheet material is a water insoluble material and the water vapor transmission rate of the sheet material is at least 200 grams per square meter per day.

43. The sheet material of claim 34, wherein the sheet material is a water insoluble material and the water vapor transmission rate of the sheet material is at least 500 grams per square meter per day.

44. The sheet material of claim 34, wherein the sheet material is a water insoluble material and the water vapor transmission rate of the sheet material is at least 1,000 grams per square meter per day.

45. A sheet material, having an average thickness of less than about ten mils, with at least a portion thereof having a generally uniform pattern of at least 1,000 thinned areas per square inch, wherein each of the thinned areas has a thickness which is at least 90 percent less than the thickness of the surrounding sheet material.

46. The thin sheet material of claim 45, wherein the area of each of the thinned microareas generally ranges from at least about 10 square micrometers to about 100,000 square micrometers.

47. The thin sheet material of claim 45, wherein the area of each of the thinned microareas generally ranges from at least about 10 square micrometers to about 1,000 square micrometers.

48. The thin sheet material of claim 45, wherein the area of each of the thinned microareas generally ranges from at least about 10 square micrometers to about 100 square micrometers.

49. The thin sheet material of claim 45, having a generally uniform pattern of at least 5,000 thinned areas per square inch.

50. The thin sheet material of claim 45, having a generally uniform pattern of at least 20,000 thinned areas per square inch.

51. The thin sheet material of claim 45, having a generally uniform pattern of at least 90,000 thinned areas per square inch.

52. The thin sheet material of claim 45, having a generally uniform pattern of at least 160,000 thinned areas per square inch.

53. The sheet material of claim 45, wherein the sheet material is a water insoluble material and the water vapor transmission rate of the sheet material is at least 200 grams per square meter per day.

54. The sheet material of claim 45, wherein the sheet material is a water insoluble material and the water vapor transmission rate of the sheet material is at least 500 grams per square meter per day.

55. The sheet material of claim 45, wherein the sheet material is a water insoluble material and the water vapor transmission rate of the sheet material is at least 1,000 grams per square meter per day.

* * * * *